US00PP37192P2

(12) United States Plant Patent
Boxriker

(10) Patent No.: US PP37,192 P2
(45) Date of Patent: Jan. 6, 2026

(54) ***OSTEOSPERMUM* PLANT NAMED 'KLEOE24785'**

(50) Latin Name: ***Osteospermum ecklonis* Norl.**
Varietal Denomination: KLEOE24785

(71) Applicant: KLEMM + SOHN GMBH & CO. KG, Stuttgart (DE)

(72) Inventor: Maike Boxriker, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/264,534

(22) Filed: Jul. 9, 2025

(51) Int. Cl.
*A01H 5/02* (2018.01)
*A01H 6/14* (2018.01)

(52) U.S. Cl.
USPC ..... Plt./360
CPC ..... *A01H 6/14* (2018.05)

(58) Field of Classification Search
USPC ..... Plt./360
CPC ..... A01H 5/02
See application file for complete search history.

*Primary Examiner* — Kent L Bell
(74) *Attorney, Agent, or Firm* — Weatherly IP Solutions, LLC; Karen P. Bechtold; James M. Weatherly

(57) ABSTRACT

A new *Osteospermum* plant particularly distinguished by about 27 inflorescences per plant and with an upright habit and good branching, is disclosed.

1 Drawing Sheet

Genus and species: *Osteospermum ecklonis* Norl.
Variety denomination: 'KLEOE24785'.

BACKGROUND OF THE NEW PLANT

The present invention comprises a new and distinct variety of *Osteospermum*, botanically known as *Osteospermum ecklonis* Norl., and hereinafter referred to by the variety name 'KLEOE24785'. 'KLEOE24785' originated from a cross-pollination conducted in summer 2019 in Stuttgart, Germany between the proprietary female *Osteospermum* variety 'OE-2015-2410' (unpatented) and the proprietary male *Osteospermum* variety 'KLEOE21535' (unpatented).

The seeds from the cross were collected and sown in January 2020 in Latina, Italy and the plants were grown for evaluation. An individual plant designated 'KLEOE24785' was selected in May 2020 in Latina, Italy. In May 2020 'KLEOE24785' was first vegetatively propagated by vegetative terminal cuttings in Latina, Italy. 'KLEOE24785' was found to reproduce true to type in successive generations of asexual propagation via vegetative cuttings.

SUMMARY

The following are the most outstanding and distinguishing characteristics of this new variety when grown under normal horticultural practices in Stuttgart, Germany.

1. About 27 inflorescences per plant;
2. Upright habit; and
3. Good branching.

DESCRIPTION OF THE PHOTOGRAPH

This new *Osteospermum* plant is illustrated by the accompanying photograph which shows a close-up of the foliage, buds, and mature inflorescences. The photograph is of an 11-week-old plant grown indoors in Stuttgart, Germany in April 2023. The colors shown are as true as can be reasonably obtained by conventional photographic procedures.

DESCRIPTION OF THE NEW VARIETY

The following detailed descriptions set forth the distinctive characteristics of 'KLEOE24785'. The data which define these characteristics were collected in Stuttgart Germany on May 14, 2025 on plants potted in Mar. 3, 2025. References are to The R.H.S. Colour Chart of The Royal Horticultural Society of London (R.H.S.), 5$^{th}$ edition (2007).

Classification:
- Family.—Asteraceae.
- *Botanical.—Osteospermum ecklonis* Norl.
- *Common.—Osteospermum.*
- *Designation.*—'KLEOE24785'.

Parentage:
- *Female parent.*—'OE-2015-2410' (unpatented).
- *Male parent.*—'KLEOE21535' (unpatented).

Plant:
- *Form and habit.*—Herbaceous perennial but usually cultivated as an annual; not frost resistant.
- *Growth habit.*—Upright.
- *Branching habit.*—Normal.
- *Height (from top of soil, including inflorescence).*—15.0 cm.
- *Width (including inflorescences).*—26.0 cm.
- *Propagation.*—Vegetative cuttings.
- *Time to produce a finished flowering plant.*—10 to 17 weeks.
- *Time to initiate and develop roots.*—4 weeks.
- *Root description.*—Fine; RHS 155A (white).

Leaves:
- *Arrangement.*—Alternate.
- *Shape.*—Obovate.
- *Apex.*—Acute.
- *Base.*—Acute.
- *Margin.*—Entire.

*Immature color*.—Upper surface: RHS 137A. Lower surface: RHS 137B.
*Mature color*.—Upper surface: RHS 137A. Lower surface: RHS 147B.
*Length*.—4.3 cm.
*Width*.—2.8 cm.
*Texture*.—Upper surface: Leathery. Lower surface: Leathery with fine hairs.
*Petioles*.—Absent.
*Venation pattern*.—Absent.

Stems:
*Total number of branches per plant* (*calculated at the base of the plant*).—5.
*Length*.—15.0 cm.
*Diameter*.—0.3 cm.
*Internode length*.—0.4 cm.
*Color*.—RHS 144C.
*Texture*.—Smooth.
*Anthocyanin*.—Absent.

Buds:
*Shape*.—Round.
*Length*.—1.0 cm.
*Diameter*.—0.7 cm.
*Color* (*at tight bud just before the ray florets unfold*) .—RHS 144A.

Inflorescence:
*Type*.—Composite, single.
*Blooming habit*.—Upright, with longer flower stems.
*Quantity of inflorescences per plant*.—27.
*Lastingness of the inflorescences on the plant*.—10 to 15 days.
*Fragrance*.—Present.
*Inflorescence diameter*.—6.5 cm.
*Inflorescence depth*.—1.4 cm.
*Disc diameter*.—1.3 cm.

Disc floret:
*Quantity per inflorescence*.—Around 30.
*Shape*.—Tubular.
*Tube color*.—Closed: RHS 37D. Mature: RHS 37D.
*Length*.—0.5 cm.
*Diameter* (*at apex*).—0.2 cm.
*Apex*.—Acute.
*Apex color*.—RHS 95C at the tips.
*Base*.—Acute.
*Base color*.—RHS 157A.
*Margin*.—Entire.

Ray floret:
*Quantity per inflorescence*.—20.
*Shape*.—Oblanceolate.
*Color*.—Upper surface: RHS NN155C, base about RHS 85B. Lower surface: RHS 85B.
*Length*.—3.2 cm.
*Width*.—1.0 cm.
*Apex*.—Obtuse.
*Base*.—Acute.
*Margin*.—Entire.
*Texture*.—Upper surface: Smooth. Lower surface: Smooth.
*Peduncle*.—Length: 2.2 cm. Diameter: 0.2 cm. Texture: Smooth with hairs. Color: RHS 144A.

Phyllaries:
*Color*.—RHS 147B.
*Arrangement*.—Single.
*Observed quantity per plant*.—17.
*Shape*.—Lanceolate.
*Color*.—Upper surface: RHS 147B. Lower surface: RHS 147B.
*Length*.—0.9 cm.
*Width*.—0.1 cm.
*Apex*.—Acute.
*Base*.—Obtuse.
*Margin*.—Entire.
*Texture*:.—Upper surface: Smooth with fine hairs. Lower surface: Smooth.

Reproductive organs:
*Androecium*.—Location: On the disc floret. Stamens: Quantity: Numerous. Shape: Filamentous. Filament length: 0.3 cm. Filament diameter: Less than 0.1 cm. Anther: Shape: Lanceolate. Color: RHS N186A. Length: 0.1 cm. Diameter: Less than 0.1 cm. Pollen: Color: RHS 17A. Amount: Moderate.
*Gynoecium*.—Location: On the base of the ray florets. Pistils: Number: Numerous. Length: 0.2 cm. Diameter: Less than 0.1 cm. Stigma: Color: RHS 157A. Shape: Filamentous. Length: 0.2 cm Diameter: Less than 0.1 cm. Style: Color: RHS 157A. Length: 0.1 cm. Diameter: 0.1 cm.

Fruit and seed set: None observed.
Disease and pest/insect resistance: None observed.

COMPARISON WITH PARENTAL LINES AND KNOWN VARIETY

'KLEOE24785' is a distinct variety of *Osteospermum* and is distinguished from its parents as described in Table 1.

TABLE 1

Comparison with Parental Lines

| Characteristic | 'KLEOE24785' | Female Parent 'OE-2015-2410' | Male Parent 'KLEOE21535' |
|---|---|---|---|
| Flower | Single | Filled | Single |
| Earliness | Medium early | Medium early | Early |

'KLEOE24785' is most similar to the commercial *Osteospermum* variety 'KLEOE24736' (unpatented). Differences between the varieties are described in Table 2.

TABLE 2

Comparison with Similar Variety

| Characteristic | 'KLEOE24785' | Commercial Variety 'KLEOE24736' |
|---|---|---|
| Habit | Upright | Compact |
| Earliness | Medium early | Medium |

I claim:

1. A new and distinct variety of *Osteospermum* plant as shown and described herein.

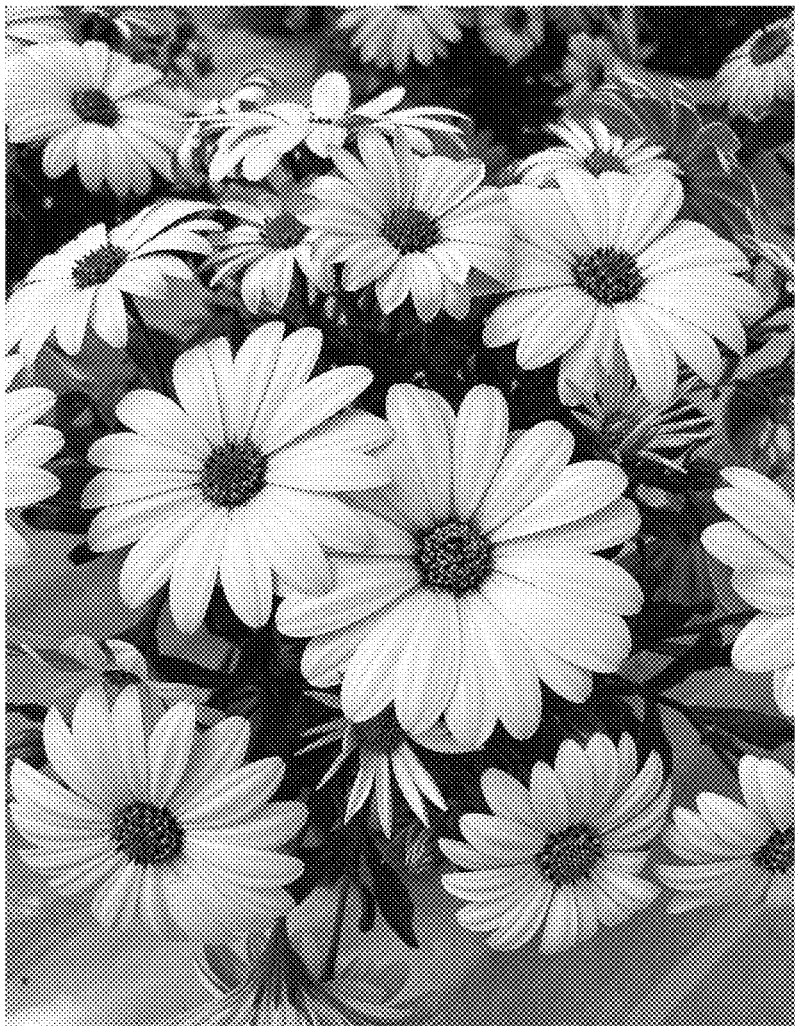

* * * * *